United States Patent
Young et al.

(10) Patent No.: US 8,052,650 B2
(45) Date of Patent: Nov. 8, 2011

(54) DEVICE WITH REMOVABLE PROJECTIONS

(75) Inventors: Ronan T. Young, Spencer, IN (US);
Mark J. Hiatt, Ellettsville, IN (US);
Andrew K. Hoffa, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 510 days.

(21) Appl. No.: 12/103,325

(22) Filed: Apr. 15, 2008

(65) Prior Publication Data

US 2008/0269686 A1    Oct. 30, 2008

Related U.S. Application Data

(60) Provisional application No. 60/926,862, filed on Apr. 30, 2007.

(51) Int. Cl.
*A61M 5/32*     (2006.01)
(52) U.S. Cl. .................................. 604/174; 604/288
(58) Field of Classification Search ...... 604/95.01–95.03, 604/516, 174, 182, 523
See application file for complete search history.

(56) References Cited

U.S. PATENT DOCUMENTS

| | | | | |
|---|---|---|---|---|
| 3,665,928 | A | * | 5/1972 | Del Guercio ............ 604/95.03 |
| 4,207,872 | A | * | 6/1980 | Meiri et al. .................. 600/116 |
| 5,037,387 | A | * | 8/1991 | Quinn et al. .................. 604/500 |
| 5,358,493 | A | * | 10/1994 | Schweich et al. ............ 604/264 |
| 5,643,320 | A | * | 7/1997 | Lower et al. .................. 606/232 |
| 6,589,213 | B2 | | 7/2003 | Reydel .......................... 604/175 |
| 6,767,339 | B2 | | 7/2004 | Reydel .......................... 604/175 |
| 2002/0082565 | A1 | * | 6/2002 | Bardani ........................ 604/239 |
| 2006/0047247 | A1 | * | 3/2006 | Anders ...................... 604/164.08 |

* cited by examiner

*Primary Examiner* — Kevin C Sirmons
*Assistant Examiner* — Brandy C Scott
(74) *Attorney, Agent, or Firm* — Brinks Hofer Gilson & Lione

(57) ABSTRACT

A feeding device configured for insertion into the gastrointestinal tract of a patient, and dynamic movement through the gastrointestinal tract toward the jejunum. The device includes an elongate tubular member having a plurality of distal projections disposed on an exterior surface thereof. The projections extend radially outwardly from the exterior surface of the tubular member a distance sufficient to engage an interior surface of the gastrointestinal tract during peristaltic contractions therein, and are configured to promote ingress of the device in response to the contractions. At least some of the projections are soluble under bodily conditions at the gastrointestinal tract, thereby facilitating removal of the feeding device.

20 Claims, 2 Drawing Sheets

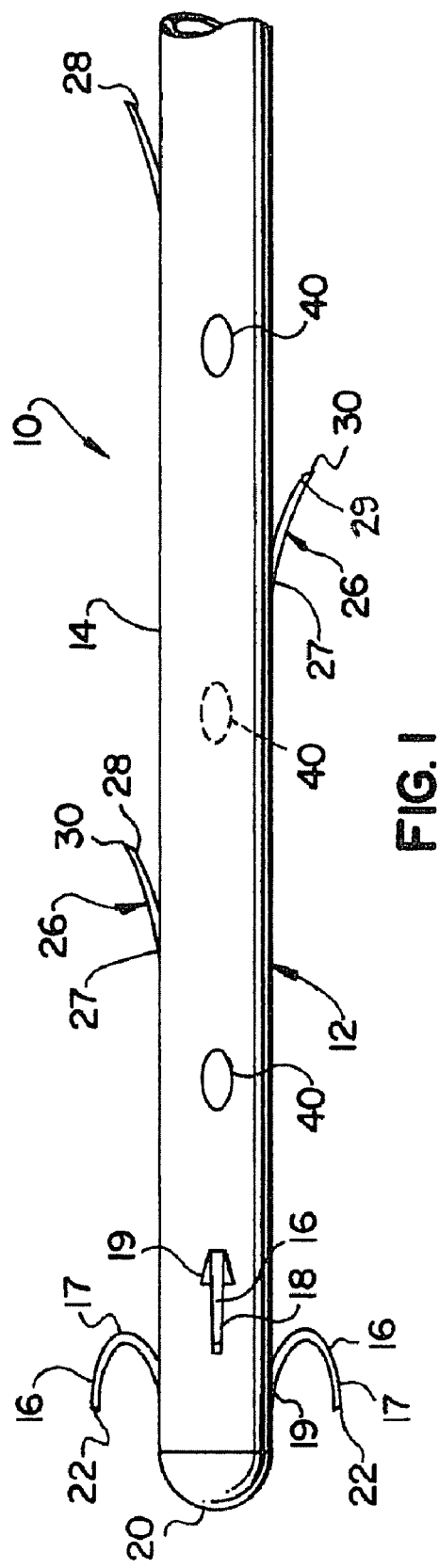

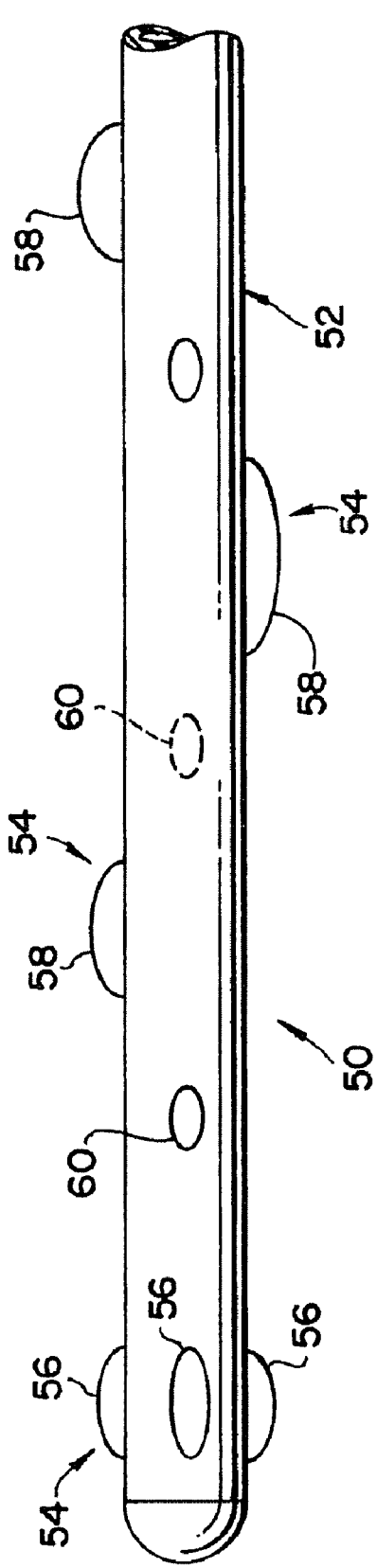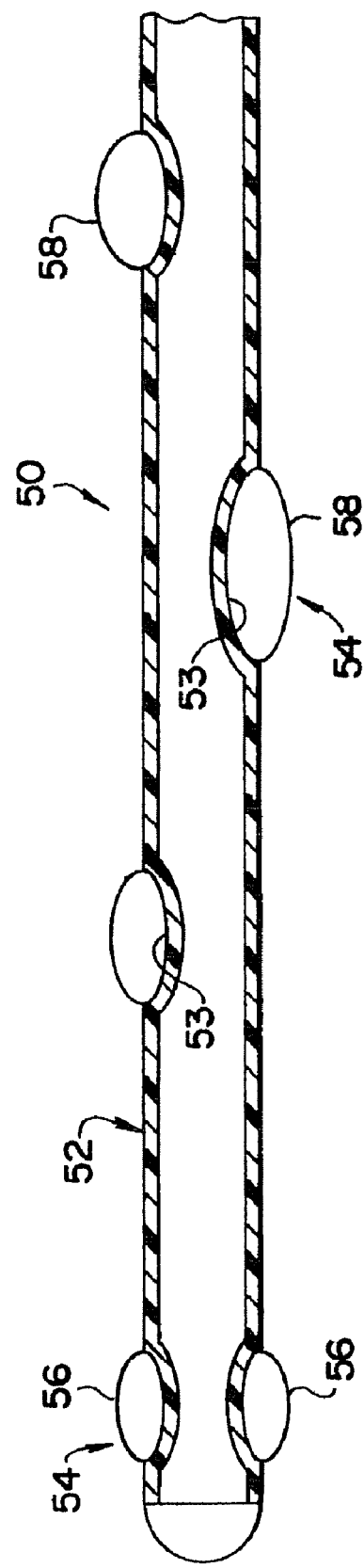

DEVICE WITH REMOVABLE PROJECTIONS

RELATED APPLICATION

The present patent document claims the benefit of the filing date under 35 U.S.C. §119(e) of Provisional U.S. Patent Application Ser. No. 60/926,862, filed Apr. 30, 2007, which is hereby incorporated by reference.

BACKGROUND OF THE INVENTION

1. Technical Field

The present invention relates to a device for invading body canals non-destructively and with a minimum of trauma. More particularly, the invention relates to a device, such as a feeding tube, having one or more removable external projections for dynamic advancement of the distal end of the device to the desired body site.

2. Background Information

Medical devices intended for non-destructive invasion of body canals have typically been provided with a low friction external surface. The low friction surface has a slippery texture to facilitate ingress of the device into the body canal for carrying out a medical procedure, and egress of the device from the body canal following termination of the procedure. Once inserted, such low friction devices were generally suitable for their intended use. However, the devices were often difficult to deliver and properly position at the desired site. In addition, insertion required a good deal of physician time and effort to insure adequate placement.

Recently, as set forth in U.S. Pat. Nos. 6,589,213 and 6,767,339, incorporated by reference herein, it was found that the ingress of the medical device or other instrumentation into a desired body site could be facilitated by providing a structure on the external surface of the device having a bi-directional coefficient of friction with respect to the tissue within the body cavity or canal that is engaged by the device during ingress. As disclosed in the incorporated-by-reference patents, the surface structure could be positioned along the device in a manner such that naturally occurring dynamic functions of the body, such as peristaltic contractions, could be used to grasp the surface structure of the device upon insertion, and carry the device toward the desired work site.

Devices such as those disclosed in the incorporated-by-reference patents have been successfully used, among others, as tubes for delivering feeding materials, drugs, contrast materials or saline, to a target site, within the body of the patient. One primary use of such devices is as jejunal feeding tubes ("J-tubes") for delivering nutritional products through the esophagus, and thereafter through the stomach or small intestine for delivery to the jejunum. Unlike conventional gastrostomy tubes ("G-tubes") that are utilized for delivery of nutritional products into the stomach, J-tubes bypass the stomach, and deposit the nutritional products directly into the jejunum (the middle section of the small intestine). Delivery of nutritional products to the jejunum is often preferred to delivery into the stomach, as it decreases the risk of adverse conditions such as gastric reflux and aspiration. In addition, in many cases, delivery directly into the jejunum provides better success in reaching patient nutritional targets, and does so at a more rapid rate than may be achieved with a conventional G-tube.

The device disclosed in the '339 patent employed a series of cilia-like flaps positioned along the external surface of the device. The flaps were positioned in a manner such that the surface could be grasped by the peristaltic contractions, and the distal end of the device propelled toward the target site.

Self-advancing tubes, such as those described in the '339 patent, are available commercially from Cook Incorporated, of Bloomington, Ind., and are sold under the trademark TIGER TUBE®. Such tubes have been well received in the medical community, and have been found to achieve a high success rate in post pyloric placement of the feeding tube.

Once successful placement is attained with the self-advancing tubes, there is little or no benefit to maintaining the surface structure, such as the flaps of the '339 patent, on the exterior of the tube. Although the flaps are generally flexible, the presence of such flaps is unnecessary when the tube is withdrawn, and the additional diameter occupied by the flaps may impose an impediment to withdrawal. It would be desirable to provide a device having surface structure suitable for enhancing advancement to the target site by peristaltic contraction, and in which the surface structure is removable following successful placement of the device.

BRIEF SUMMARY

The present invention addresses the shortcomings of the prior art. In one form thereof, the invention comprises a medical device configured for dynamic movement through a body canal toward an interior target site and removal therefrom. The device includes an elongate tubular member having a plurality of distal projections disposed on an exterior surface thereof. The projections extend outwardly from the exterior surface of the tubular member a distance sufficient to engage an interior surface of the body canal during bodily contractions therein. The distal projections are configured to promote ingress of the device in response to the contractions. At least some of the projections are formed of a composition that is soluble under bodily conditions encountered at the body canal.

In another form thereof, the invention comprises a nasojejunal feeding device for insertion into a patient. The feeding device is configured for dynamic movement into and through the patient's gastrointestinal tract toward an internal target site at the jejunum of the patient. The feeding device includes a hollow tubular member having a distal portion and an outer surface, wherein a plurality of flaps is disposed on the outer surface at the distal portion. The flaps project outwardly from the surface of the tubular member so as to engage an interior surface of the gastrointestinal tract, and are configured so as to promote ingress of the feeding tube toward the jejunum in response to peristaltic contractions. The flaps are formed of a material that dissolves when the tubular member is received in the gastrointestinal tract. The tubular member further includes a plurality of apertures sized and shaped to permit fluid-like materials to enter the jejunum from the interior of the tubular member.

In still another form thereof, the invention comprises a medical device configured for dynamic movement through a body canal toward an interior target site and removal therefrom. The device includes an elongate tubular member having a plurality of distal projections disposed on an exterior surface thereof. The projections extend radially outwardly from the exterior surface of the tubular member a distance sufficient to engage an interior surface of the body canal during bodily contractions therein. The distal projections are configured so as to promote ingress of the device in response to the contractions. At least some of the projections are removable from the elongate tubular member under bodily conditions at the body canal for facilitating removal of the feeding device from the target site.

BRIEF DESCRIPTION OF THE DRAWINGS

FIG. 1 is a side view of the distal portion of a device according to an embodiment of the present invention;

FIG. 2 is a side view of the device of FIG. 1, following dissolution of the side flaps;

FIG. 3 is a side view of the distal portion of an alternative embodiment of a device according to the present invention; and FIG. 4 is a longitudinal sectional view of the device of FIG. 3.

DESCRIPTION OF THE PREFERRED EMBODIMENTS

For purposes of promoting an understanding of the present invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the inventive device, as well as the axial ends of various component features of the device. The term "proximal" is used in its conventional sense to refer to the end of the device (or component thereof) that is closest to the operator during use of the device. The term "distal" is used in its conventional sense to refer to the end of the device (or component thereof) that is initially inserted into the patient, or that is closest to the patient during use.

FIG. 1 illustrates a side view of the distal portion of a device 10, according to an embodiment of the present invention. In this embodiment, device 10 is fashioned as a feeding tube, such as a naso-jejunal tube, for delivering nutritional products directly into the jejunum of a patient. Those skilled in the art will appreciate that the described use of device 10 herein as a feeding tube is exemplary only, and that additional uses may be made for device 10. For example, in addition to nutritional products, device 10 may be used for delivering other fluid-like materials such as drugs, contrast materials or saline to target sites in the patient. Device 10 may also be used as a feeding tube for other than naso-jejunal feeding, and/or may be used for delivery of specified materials to target sites in other body canals. All such uses are considered within the scope of the invention.

Only the distal portion of device (feeding tube) 10 is depicted in the figures. The proximal portions of such devices are conventional, and further description of the proximal portion is not necessary for an understanding of the features of the present invention. In a preferred embodiment, an 8 to 16 French tube is utilized, having a minimum overall length of about 154 cm. Those skilled in the art will appreciate that these dimensions, as well as other dimensions recited herein, are exemplary only, and that other dimensions may be appropriate for a particular case. Typically, such tubes are formed of a flexible polymeric composition, such as PVC or polyurethane. Other flexible elastomeric compositions, such as silicone, may alternatively be utilized in a particular case.

In the non-limiting embodiment shown, device 10 is fashioned generally similar to the feeding tube described in the incorporated by reference '339 patent. Device 10 comprises an elongated tubular member 12 having a plurality of projections extending radially from the external surface of the tubular member. In the embodiment of FIG. 1, the projections comprise a series of generally cilia-like flaps 16, 26 adhered to the outer surface 14 of the tubular member. A plurality (such as four) of distal flaps 16 are disposed about the perimeter of the distal end portion of outer surface 14 at approximately equal intervals (i.e., at 90° intervals), and are positioned near the distal tip 20 of tubular member 12. In the embodiment shown, the distal flaps 16 comprise a first oppositely disposed pair of distal flaps 17 located, e.g., about 0.7 cm from the distal tip 20 of device 10, and a second oppositely disposed pair of distal flaps 18 located, e.g., about 1.0 cm from the distal tip 20 of device 10, as measured from the base 19 of each of the flaps 17, 18. When straightened, each of the distal flaps is approximately 1 cm in length.

Flaps 16 are configured to cause device 10 to be propelled forwardly by naturally occurring contractions of the tissue of the body canal, and to resist egress of the device. In particular, when the device 10 is being inserted into the body canal, the distal flaps 16 provide a relatively large diameter near the closed distal tip 20 of the device that can be readily grasped by the tissue of the body canal during peristaltic contractions.

A plurality of secondary flaps 26 is disposed along the outer surface 14 of tubular member 12 proximal of the distal tip 20 and the distal flaps 16. The secondary flaps 26 preferably alternate along opposite sides of the device at approximately 2 cm intervals. Thus, the secondary flaps 26 comprise a first series of secondary flaps 28 disposed along the top side of the device (as viewed in FIG. 1) and spaced at approximately 4 cm intervals, and a second series of secondary flaps 29 disposed along the bottom side of the device (as viewed in FIG. 1) and spaced at approximately 4 cm intervals.

In the preferred embodiment, each of the secondary flaps 26 measures approximately 0.5 cm in length when straightened. Each of the secondary flaps 26 preferably has a truncate shape comprising a base 27 measuring approximately 0.016 cm in width, and a tip 30 measuring approximately 0.010 cm in width. Preferably, each of the secondary flaps 26 is moderately curved outwardly so as to prevent the secondary flaps 26 from adhering to the outer surface 14 of tubular member 12, and to allow the tip 30 to engage the tissue of the body canal (not shown). The secondary flaps 26 are also preferably configured to orient the secondary flap tips 30 rearwardly (i.e., away from the distal tip 20 of the device 10). This rearward orientation of the secondary flaps 26 causes device 10 to be propelled forwardly by the naturally occurring peristaltic contractions of the tissue of the body canal during the insertion process, and also resists egress of the device. The secondary flaps 26 are also sufficiently flexible to prevent trauma to the tissue of the body canal during insertion of device 10.

Preferably, flaps 16, 26 are distributed along the distal 50 cm of device 10. In the embodiment shown, device 10 further comprises a plurality of apertures 40 also disposed along the distal portion of elongated tubular member 12. Apertures 40 preferably measure about 0.5 cm in diameter, and provide openings through which feeding material or other fluids can exit the interior of the device and enter the body canal or cavity. In the embodiment shown, the apertures 40 are alternately disposed along opposite sides of the device, and are preferably located along the sides of the device that are 90° offset from the sides of the device along which the secondary flaps 26 are located (i.e., along the front and back sides of the device as viewed in FIG. 1).

Providing a device, such as a feeding tube, with a plurality of flaps enhances the dynamic movement of the device within the body canal. The flaps are positioned along the surface of the device in a manner such that the naturally occurring peristaltic contractions grasp the flaps upon insertion, and carry the distal end of the device into the jejunum. As such, the flaps provide a very convenient manner of inserting the device, and directing its distal tip to the target site, by utilizing natural body contractile functions.

It is, of course, apparent that at some point the device will have to be removed from the body canal. Typically, removal will occur upon completion of the medical procedure for which the device has been inserted, such as enteral feeding. Although the flaps 16, 26 are beneficial for propelling the device forward during peristaltic contractions as described, they do not contribute to the removal of the device following termination of the procedure. During removal ("egress"), the device is withdrawn in a direction opposite to that urged by the peristaltic contractions. In this case, any grasping or contractile effect is counterproductive to smooth removal of the device. In addition, the additional diameter occasioned by the presence of the flaps may impose an impediment to withdrawal.

In a preferred embodiment of the present invention, flaps 16, 26 are formed of a composition that is soluble under the conditions to which the device is exposed in the body canal. Thus, for example, when device 10 is a naso-jejunal feeding tube, flaps 16, 26 are formed of a composition that is soluble under conditions encountered in the lower part of the digestive tract (i.e., the gut). As a result, at some point following insertion of the device, flaps 16, 26 dissolve and are no longer present along the outer surface of device 10. This eliminates a potential impediment to removal of the device during egress, and facilitates smooth withdrawal. FIG. 2 illustrates the profile of device 10 following dissolution of the flaps (the original positioning of flaps 16, 26 is shown in phantom).

Although in the preferred embodiment described herein, all of flaps 16, 26 are formed of a soluble composition as described, this need not be the case in each and every instance. Rather, if desired, in some instances one or more flaps need not necessarily be formed of the soluble composition. However, it is believed that the benefits of the invention are best achieved when most, if not all, of flaps 16, 26 are soluble or otherwise capable of removal as described herein.

In order to enhance dissolution, flaps 16, 26 may be formed of a biosoluble plastic. Non-limiting examples of plastics suitable for a particular use include poly(dl-lactide) (DL-PLA); poly(l-lactide) (LPLA); polyglycolide (PGA); poly(dioxanone) (PDO); poly(glycolide-co-trimethylene carbonate) (PGA-TMC); poly(l-lactide-co-glycolide) (PGA-LPLA); poly(dl-lactide-co-glycolide) (PGA-DLPLA); poly(l-lactide-co-dl-lactide) (LPLA-DLPLA); and poly(glycolide-co-trimethylene carbonate-co-dioxanone) (PDO-PGA-TMC). This listing of suitable biosoluble compositions is not intended to be complete, and those skilled in the art will appreciate that other biosoluble compositions may be substituted for the compositions listed above, depending upon the intended use of device 10 and the body canal in which it is inserted.

Flaps 16, 26 may be attached to device 10 by any suitable means depending upon the compositions of device 10 and the flaps. Thus, for example, flaps 16, 26 may be adhered to the external surface of tubular member 12 using an appropriate biocompatible adhesive. As another example, flaps 16, 26 can be molded onto the surface of the tubular member. Those skilled in the art will appreciate that other suitable mechanisms for attaching structures may be substituted, depending upon the compatibility of the tubular member and the flaps.

In the preferred embodiment described and illustrated above, the projections extending from the external surface of tubular member 12 comprise a series of flaps 16, 26 distributed along the distal length of device 10. As stated, in the non-limiting embodiment shown, flaps 16, 26 are distributed essentially in the same general manner as the flaps in the incorporated-by-reference '339 patent. This arrangement has been found to be very effective in promoting contractions, such as peristalsis, in commercially available tubes, such as the aforementioned TIGER TUBE®. However, the flaps in the incorporated-by-reference patent are not indicated as being dissolvable or otherwise removable for enhancing withdrawal of the device.

Those skilled in the art will appreciate that the arrangement of the projections, such as flaps 16, 26 described hereinabove, along the external surface of the elongated tubular member is merely one example of suitable projections. Numerous alternative arrangements may also be effective for the described purposes, all such arrangements being considered within the scope of the invention. For example, it is not necessary to have two distinct sets of flaps 16, 26 with different configurations. Rather, all flaps can have the same configuration, which need not necessarily be either of the configurations described herein. Similarly, it is not necessary for flaps 16, 26 to be distributed along the surface of the distal end of device 10 in the configuration described. Rather, in some cases, random, spiral, etc. configurations will be satisfactory. Since the purpose of the radial projections (e.g., flaps) is to provide a grasping surface for the bodily contractions, a virtually unlimited number of arrangements could be fashioned to facilitate insertion of the device via such contractions, the examples provided herein merely representing one suggested arrangement for a particular use.

Although the examples provided hereinabove describe the external projections as a series of flaps, those skilled in the art will appreciate that other structures may also be fashioned to enhance dynamic advancement of the device by bodily contractions, and are also within the scope of the invention. FIG. 3 illustrates a device 50 comprising an elongated tubular member 52 and a series of mounds 54 positioned along the external surface of tubular member 52. In the embodiment of FIG. 3, mounds 54 can comprise a series of distal mounds 56 and secondary mounds 58, positioned as in the previous embodiment with the flaps. Mounds 54 can be formed of the compositions described above for flaps 16, 26, or any other compositions that are suitable for attachment to tubular member 52, and that are capable of dissolving under the conditions in the body canal in which device 50 is inserted. Device 50 may also include apertures 60 for transmission of fluid products from the inside of tubular member 52 to the environment exterior of device 50.

Mounds 54 may alternatively be positioned along the external surface of tubular member 52 in any other configuration, such as a spiral or a random configuration, suitable for insertion of device 50 by bodily contractions as described. Mounds 54 may be adhered or otherwise attached to the outer surface of tubular member 52, or can be formed to project outwardly (radially) from respective grooves 53 (FIG. 4) formed in the outer surface of tubular member 52.

In addition to the specific external projections described and illustrated herein (flaps and mounds), those skilled in the art will appreciate that the projections may alternatively comprise any other size, shape and orientation suitable for the intended purpose. Thus, for example, the projections can comprise a series of bumps, ribs or ridges along the outer surface of the tubular portion of the inventive device. The projections likewise need not all be of the same type. Thus, for example, the projections may comprise combinations of flaps, mounds, bumps, etc., distributed along the external surface of the tubular member in a manner to promote ingress resulting from bodily contractions. The skilled artisan can readily determine an optimal configuration and arrangement of projections from the surface of the device for a particular intended use when following the teachings of this invention.

Those skilled in the art will appreciate that the external projections need not necessarily be formed of a composition that is soluble under the conditions encountered within the body canal. Although removing the projections by dissolution in the canal represents one preferred embodiment, other methods of removing the projections are also possible, and are considered within the scope of the invention. For example, the projections may be engaged with the outer surface of the tubular member in a manner such that they are capable of disengagement therefrom by the time that the device is to be withdrawn. As one example, the projections can be formed of a nonsoluble composition, e.g., of the same or a similar composition as that of the tubular member. These projections can then be adhered (e.g., by a soluble adhesive such as cyanoacrylate) or otherwise engaged (e.g., by dissolvable sutures) to the outer surface of the tubular member. In this instance the adhesive or other dissolvable structure dissolves prior to withdrawal of the device. For applications such as in the gastrointestinal tract, these nonsoluble external projections will simply pass as free floating structures through the gastrointestinal tract after disengaging from the tubular structure. If the device is to be used in body canals other than the gastrointestinal tract, the medical professional must, of course, consider the feasibility of allowing a free floating projection member to pass through the particular canal.

When selecting a particular composition for the dissolvable projection, adhesive, etc., for use in the invention, one should consider the length of time that is typically required for the device to be fully passed through the body canal by the contractions to the intended target site. Thus, for example, when a feeding device is configured for dynamic movement through the patient's gastrointestinal tract by peristaltic contraction, it is known that the device will often take between 5 and 15 hours for movement through the GI tract and proper seating of the distal end of the device in the jejunum. As a rough rule of thumb, such devices may advance about 10 cm per hour through the tract. The feeding device may be left in place as long as necessary for providing nutrition to the patient, with such indwelling time usually not exceeding about sixty days. The dissolvable projection and/or adhesive should be selected such that it does not dissolve in a shorter time period than that required for proper seating of the device in the canal, but wherein it is at least partially, if not fully, dissolved prior to withdrawal of the device.

While these features have been disclosed in connection with the illustrated preferred embodiments, other embodiments of the invention will be apparent to those skilled in the art that come within the spirit of the invention as defined in the following claims.

What is claimed is:

1. A medical device configured for dynamic movement through a body canal toward an interior target site and removal therefrom, said device comprising an elongate tubular member having a plurality of distal projections disposed on an exterior surface thereof, said projections extending outwardly from the exterior surface of the tubular member a distance sufficient to engage an interior surface of the body canal during bodily contractions therein, said distal projections being configured so as to promote ingress of said device in response to said contractions, at least some of said projections being formed of a composition that is soluble under bodily conditions at said body canal.

2. The device of claim 1, wherein said distal projections comprise a series of flaps along said external surface.

3. The device of claim 2, wherein said series of flaps comprises a plurality of distal flaps arranged near a distal tip of said tubular member, and a series of secondary flaps arranged proximal to said distal flaps, said secondary flaps having a configuration different than said distal flaps.

4. The device of claim 3, wherein said distal flaps and said secondary flaps comprise tips that are oriented in opposite directions.

5. The medical device of claim 1, further comprising a series of apertures along the surface of said tubular member.

6. The medical device of claim 1, wherein said distal projections are formed from at least one of poly(dl-lactide) (DL-PLA); poly(I-lactide) (LPLA); polyglycolide (PGA); poly(dioxanone) (PDO); poly(glycolide-co-trimethylene carbonate) (PGA-TMC); poly(l-lactide-co-glycolide) (PGA-LPLA); poly(dl-lactide-co-glycolide) (PGA-DLPLA); poly(l-lactide-co-dl-lactide) (LPLA-DLPLA); and poly(glycolide-co-trimethylene carbonate-co-dioxanone) (PDO-PGA-TMC).

7. The medical device of claim 1, wherein the distal projections are adhered to the surface of the tubular member.

8. The medical device of claim 1, wherein the distal projections are molded to the surface of the tubular member.

9. The medical device of claim 1, wherein the exterior surface of said tubular member includes a plurality of grooves, and wherein said distal projections extend radially outwardly from said grooves.

10. The medical device of claim 1, wherein said tubular member comprises PVC, polyurethane or silicone.

11. A naso-jejunal feeding device for insertion into a patient, said feeding device configured for dynamic movement into and through the patient's gastrointestinal tract toward an internal target site at the jejunum of the patient, the feeding device comprising: a hollow tubular member having a distal portion and an outer surface; a plurality of flaps disposed on said outer surface at said distal portion, said flaps projecting outwardly from the surface of the tubular member so as to engage an interior surface of the gastrointestinal tract and configured so as to promote ingress of the feeding tube toward said jejunum in response to peristaltic contractions;

said flaps being formed of a material that dissolves when said tubular member is received in the gastrointestinal tract, said tubular member further comprising a plurality of apertures sized and shaped to permit fluid-like materials to enter the jejunum from an interior space of said tubular member.

12. The naso-jejunal feeding device of claim 11, wherein said flaps are formed from at least one of poly(dl-lactide) (DLPLA); poly(I-lactide) (LPLA); polyglycolide (PGA); poly(dioxanone) (PDO); poly(glycolide-co-trimethylene carbonate) (PGA-TMC); poly(l-lactide-co-glycolide) (PGA-LPLA); poly(dl-lactide-co-glycolide) (PGA-DLPLA); poly(l-lactide-co-dl-lactide) (LPLA-DLPLA); and poly(glycolide-co-trimethylene carbonate-co-dioxanone) (PDO-PGA-TMC).

13. The naso-jejunal feeding device of claim 11, wherein said flaps comprise respective first and second sets of flaps disposed along said outer surface, said flaps of said first set having a shape, size and orientation that is different from said flaps of said second set, each of said flaps being configured to promote said ingress in response to peristaltic contractions.

14. The naso-jejunal feeding device of claim 13, wherein said first set of flaps comprise tips that are oriented in a different direction than tips of said second set of flaps.

15. A medical device configured for dynamic movement through a body canal toward an interior target site and removal therefrom, said device comprising an elongate tubular member having a plurality of distal projections disposed on an exterior surface thereof, said projections extending radially outwardly from the exterior surface of the tubular member a distance sufficient to engage an interior surface of the body canal during bodily contractions therein, said distal projections being configured so as to promote ingress of said device in response to said contractions, at least some of said projections being removable from said elongate tubular member under bodily conditions at said body canal for facilitating removal of said feeding device from said target site.

16. The medical device of claim 15, wherein said projections are soluble under said conditions at said body canal.

17. The medical device of claim 15, further comprising an adhesive for adhering said at least some distal projections to said tubular member exterior surface, said adhesive being soluble under said conditions at said body canal, such that said adhered projections are removable from said device upon dissolution of said adhesive.

18. The medical device of claim 15, wherein the exterior surface of said tubular member includes a plurality of grooves, and wherein distal projections extend radially outwardly from said grooves.

19. The medical device of claim 15, wherein said projections comprise mounds projecting from said exterior surface.

20. The medical device of claim 15, wherein said tubular member and said mounds comprise at least one of PVC, polyurethane and silicone.

* * * * *